United States Patent [19]

Barber et al.

[11] Patent Number: 5,776,972

[45] Date of Patent: Jul. 7, 1998

[54] KAPPA-OPIATE AGONISTS FOR INFLAMMATORY BOWEL DISORDERS

[75] Inventors: Andrew Barber, Weiterstadt; Christoph Seyfried, Seeheim; Gerd Bartoszyk, Weiterstadt; Rudolf Gottschlich, Reinheim, all of Germany

[73] Assignee: Merck Patent Gesellschaft mit Beschrankter Haftung, Germany

[21] Appl. No.: 671,502

[22] Filed: Jun. 27, 1996

[30] Foreign Application Priority Data

Jun. 28, 1995 [DE] Germany ................ 195 23 502.9

[51] Int. Cl.$^6$ .................................................. A61K 31/40
[52] U.S. Cl. .................. 514/424; 514/428; 548/556; 548/567; 548/568
[58] Field of Search ............... 548/556, 567, 548/568; 514/424, 428

[56] References Cited

U.S. PATENT DOCUMENTS

| | | | |
|---|---|---|---|
| 4,663,343 | 5/1987 | Horwell et al. | 514/429 |
| 5,232,266 | 8/1993 | Gottschlich et al. | 514/428 |
| 5,232,978 | 8/1993 | Gottschlich et al. | 514/422 |
| 5,532,266 | 7/1996 | Gottschlich et al. | 514/428 |

OTHER PUBLICATIONS

R. Gottschlich, K.A. Ackermann, A. Barber, G.D. Bartoszyk, H.E. Greiner Bioorganic & Medicinal Chemistry, vol. 4, No. 5, pp. 677–682, 1994.

Issselbacker et al. "Harrison's Principles of internal medicine" vol. 2, Thirteenth edition, 1403–1417, 1994.

Roger et al. Can. J. Vet. Res. vol. 58 (3), 163–166, 1994.

Upton et al. European Journal of Pharmacology, 78 (4), 412–429, 1982.

Ramabadran K. European Journal of Pharmacology, 98 (3–4), 425–427, 1984.

Bhargava et al. Brain Research, 625 (1), 120–124, 1993.

Barber et al., "A pharmacological provile of the novel, peripherally-selective . . . ", Br. J. Pharmacol. (1994), 113, 1317–1327.

Gottschlich et al., "K–Opioid Activity of the Four Stereoisomers . . . ", Chriality 6: 685–689 (1994).

Gottschlich et al., "The peripherally acting K–opiate agonist EMD . . . ", Drugs Exptl. Clin. Res., XX(5), 171–174, (1995).

*Primary Examiner*—Mukund J. Shah
*Assistant Examiner*—Bruck Kifle
*Attorney, Agent, or Firm*—Millen, White, Zelano & Branigan, P.C.

[57] ABSTRACT

Pharmaceutical preparations which are suitable for the treatment of inflammatory bowel disorders and contain at least one compound of the formula I

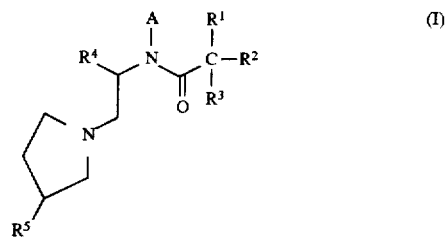

in which $R^1$ is Ar, cycloalkyl having 3–7 C atoms or cycloalkylalkyl having 4–8 C atoms, $R^2$ is Ar, or $R^1$ and $R^2$ together are

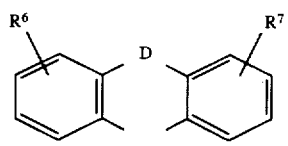

$R^3$ is H, OH, OA or A, $R^4$ is A or phenyl which can optionally be mono- or disubstituted by Hal, OH, OA, $CF_3$, $NO_2$, $NH_2$, NHA, NHCOA, $NHSO_2A$ and/or $NA_2$, $R^5$ is OH, $CH_2OH$, $R^6$ and $R^7$ in each case independently of one another are H, Hal, OH, OA, $CF_3$, $NH_2$, NHA, $NA_2$, NHCOA, $NHCONH_2$, $NO_2$ or methylenedioxy, with the oxy groups bonded to adjacent carbons on the ring, A is alkyl having 1–7 C atoms, Ar is a mono- or bicyclic aromatic radical which can optionally contain an N, O or S atom in the ring and can be mono-, di- or trisubstituted by A, Hal, OH, OA, $CF_3$, $NH_2$, NHA, $NA_2$, NHCOA and/or $NHCONH_2$, D is $CH_2$, O, S, NH, NA, —$CH_2$—$CH_2$—, —CH=CH—, —$CH_2$—NH—, —$CH_2$—NA— or a bond and Hal is F, Cl, Br or I; and/or physiologically acceptable salts and/or one of its glycosylated derivatives , and at least one physiologically acceptable excipient or auxiliary.

6 Claims, No Drawings

KAPPA-OPIATE AGONISTS FOR INFLAMMATORY BOWEL DISORDERS

The invention relates to pharmaceutical preparations which are suitable for the treatment of inflammatory bowel disorders and contain at least one compound of the formula I

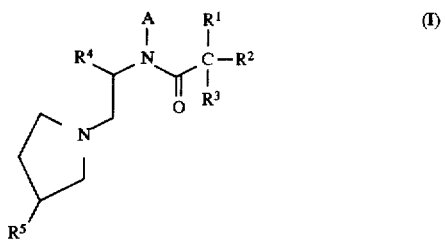

in which

R$^1$ is Ar, cycloalkyl having 3–7 C atoms or cycloalkylalkyl having 4–8 C atoms, R$^2$ is Ar, R$^1$ and R$^2$ together may also be

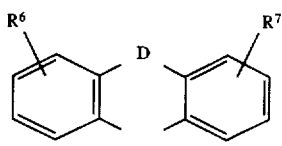

R$^3$ is H, OH, OA or A,

R$^4$ is A or phenyl which can optionally be mono- or disubstituted by Hal, OH, OA, CF$_3$, NO$_2$, NH$_2$, NHA, NHCOA, NHSO$_2$A and/or NA$_2$, R$^5$ is OH, CH$_2$OH, R$^6$ and R$^7$ in each case independently of one another are H, Hal, OH, OA, CF$_3$, NH$_2$, NHA, NA$_2$, NHCOA, NHCONH$_2$, NO$_2$ or methylenedioxy, with the oxy groups bonded to adjacent carbons on the ring, A is alkyl having 1–7 C atoms, Ar is a mono- or bicyclic aromatic radical which can optionally contain an N, O or S atom in the ring and can be mono-, di- or trisubstituted by A, Hal, OH, OA, CF$_3$, NH$_2$, NHA, NA$_2$, NHCOA and/or NHCONH$_2$, D is CH$_2$, O, S, NH, NA, —CH$_2$—CH$_2$—, —CH=CH—, —CH$_2$NH—, —CH$_2$—NA— or a bond and Hal is F, Cl, Br or I; and/or one of its physiologically acceptable salts and/or one of its glycosylated derivatives, and at least one physiologically acceptable excipient or auxiliary.

BACKGROUND OF THE INVENTION

Compounds with a similar structural formula and suitable processes for their preparation are described in the Offenlegungsschrift DE 40 34 785.

Inflammatory bowel disorders frequently lead to colonic pain, digestive disorders and in the worst case to intestinal obstruction. The latter is associated with colic-like pain as a result of a heavy contractile stimulus, stool and wind retention, vomiting and, with increasing duration of the condition, dehydration, rebound tenderness of the abdomen and finally shock.

Functional bowel disorders are attributed to all sorts of causes; inter alia to an abnormality in the contractility of the smooth intestinal muscles and the gastrointestinal motor activity. An excessive contractile activity and a modified coordination of the motor activity can cause pain by the activation of the mechanico-receptor and by transport abnormalities which lead to distension of the intestine. These causes were until now also assumed to explain chest pains which are not due to the heart, and also to explain the pain of irritable bowel syndrome or dyspepsia which is not associated with an ulcer. Meanwhile, this relationship has been further supported by 24-hour recordings of the motor oesophageal and gastroduodenal function of patients who were suffering from chest pain which was not due to the heart or dyspepsia which was not associated with an ulcer (Katz, P. O. et al. Ann. Intern. Med. (1987) 106, 593-7). Motor abnormalities can occur in normal controls without symptoms, but can also disappear, whereby a temporal correlation can be shown with the symptoms of the patient (Fefer, L. et al. Gastroenterology (1992) 102: A447 (Abstract)).

The treatment of the motor abnormalities with all sorts of therapeutically active agents, for example with agents which promote the motions of the gastrointestinal tract, with anticholinergics or calcium channel and cholecystokinin antagonists, are in most cases effective in the correction of the motor abnormalities, but they do not always improve the symptoms of the patients.

SUMMARY OF THE INVENTION

It was therefore an object of this invention to make available pharmaceutically active compounds which can be employed and are effective in the treatment of inflammatory bowel disorders, which simultaneously alleviate the pain associated with this disorder and in the acute case of an intestinal obstruction which is threatened or produced by the inflammatory bowel disorder normalize the motoricity of the intestine again or set it going again without causing noticeable side effects. At the same time, it was an object of the invention to make available pharmaceutically active compounds which have no effects on normal intestinal peristalsis, but additionally cause the healing of the inflammatory bowel disorder.

Upon further study of the specification and appended claims, further objects and advantages of this invention will become apparent to those skilled in the art.

It has now been found that compounds of the formula I

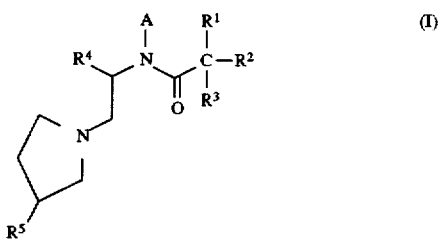

in which

R$^1$ is Ar, cycloalkyl having 3–7 C atoms or cycloalkylalkyl having 4–8 C atoms, R$^2$ is Ar, $R^1$ and $R^2$ together may also be

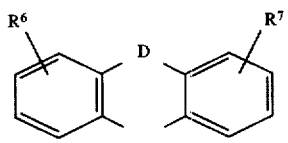

$R^3$ is H, OH, OA or A, $R^4$ is A or phenyl which can optionally be mono- or disubstituted by Hal, OH, OA, $CF_3$, $NO_2$, $NH_2$, NHA, NHCOA, $NHSO_2A$ and/or $NA_2$, $R^5$ is OH, $CH_2OH$, $R^6$ and $R^7$ in each case independently of one another are H, Hal, OH, OA, $CF_3$, $NH_2$, NHA, $NA_2$, NHCOA, $NHCONH_2$, $NO_2$ or methylenedioxy with the oxy groups bonded to adjacent carbons on the ring, A is alkyl having 1–7 C atoms, Ar is a mono- or bicyclic aromatic radical which can optionally contain an N, O or S atom in the ring and can be mono-, di- or trisubstituted by A, Hal, OH, OA, $CF_3$, $NH_2$, NHA, $NA_2$, NHCOA and/or $NHCONH_2$, D is $CH_2$, O, S, NH, NA, $-CH_2-CH_2-$, $-CH=CH-$, $-CH_2NH-$, $-CH_2-NA-$ or a bond and Hal is F, Cl, Br or I, and/or one of its physiologically acceptable salts, but in particular compounds of the formula I in which Ar is phenyl, $R^3$ is H, and A is methyl, are pharmaceutically active compounds which are very particularly suitable as medicaments for the treatment of inflammatory bowel disorders. It has been found that particularly active compounds for the treatment of corresponding disorders are present if $R^5$ is an OH group and $R^1$ and $R^2$ in each case are Ar. Very particularly active in this respect is a compound of the formula I in which $R^1$, $R^2$ and $R^4$ are phenyl, A is methyl and $R^5$ is OH.

The invention thus relates, in addition to the compounds of the formula I and their use as medicaments for the treatment of inflammatory bowel disorders, also to preparations which comprise compounds of the formula I as a constituent of pharmaceutical preparations and can therefore be employed for the effective treatment of inflammatory bowel disorders and the symptoms associated therewith, and also for the treatment of severe pain, in particular of hypersensitivity to pain.

The invention likewise relates to the use of the compounds of the formula I as medicaments for the treatment of pain and hypersensitivity to pain occurring in myelopathy, burn injuries, sunburn and rheumatic disorders, and inflammatory reactions occurring in this context. The invention also relates to the use of these medicaments for the treatment of postoperative pain, hypersensitivity reactions to pain, and the ileus frequently occurring after abdominal operations. The invention further relates to the use of the corresponding compounds in pharmaceutical formulations for the treatment of neurodermatitis.

As already mentioned above, compounds having a similar structural formula and their preparation are disclosed per se in the Offenlegungsschrift DE 40 34 785. The therapeutic action of the compounds described herein is not known.

Compounds of the formula I and their physiologically acceptable salts exhibit particularly good analgesic actions.

In this connection, they antagonize, in particular, inflammation-related hyperalgesias, but are also effective in the control of the actual inflammatory event, so that they have a broad spectrum of action.

Experiments have shown that the compounds according to the invention are active in the "writhing test" on mice or rats (method cf. Siegmund et al., Proc. Soc. Exp. Biol. 95, (1957), 729–731). The analgesic action as such can be further detected in the "tail-flick test" on mice or rats (methodology cf. d'Amour and Smith, J. Pharmacol. Exp. Ther. 72, (1941), 74–79) and further in the "hot plate test" (cf. Schmauss and Yaksh, J. Pharmacol. Exp. Ther. 228, (1984), 1–12 and the literature cited there). Particularly strong actions are to be observed on rats in the carrageenan-induced hyperalgesia model (cf. Bartoszyk and Wild, *Neuroscience Letters* 101 (1989) 95). In this context, the compounds show no or only a small tendency to physical dependence.

Additionally, by means of corresponding experiments carried out by familiar methods, pronounced anti-inflammatory, diuretic, anticonvulsive and neuro-protective actions were demonstrated. The compounds exhibit a high affinity with respect to the binding behavior to kappa-receptors.

In contrast to other compounds having a similar spectrum of action, compounds of the formula I are particularly suitable for use in pharmaceutical preparations for the treatment of inflammatory bowel disorders, as in addition to the analgesic and anti-inflammatory action they are suitable for normalizing disorders of the intestinal motoricity produced by the disorder. In particular, they are suitable for getting the bowel movements going again if, due to the inflammatory bowel disorder, intestinal obstruction threatens or has already occurred. This action can also be employed for the treatment of postoperative ileus and the pain associated therewith.

On account of the pharmacological activity described above, these compounds have proved particularly suitable in the treatment of burns, namely both of burns due to the action of heat or flames and also of severe sunburns. In particular, in addition to the actual pain and hypersensitivity reactions to pain, inflammatory processes can additionally be influenced in these indications by the administration of suitable pharmaceutical preparations which comprise the active compounds according to the invention. Also, the reflex ileus occurring in the case of the most severe burns can be prevented or treated.

In this connection, indications have also been found which point to an advantageous action in the treatment of allergies to the sun, especially as under the influence of the compounds of the formula I according to the invention allergic skin reactions rapidly fade and the itching associated therewith rapidly subsides. Corresponding positive results were also found in the treatment of neurodermatitis. In particular, the itching of the skin and inflammatory reactions occurring due to the disorder are favorably influenced, even in this disorder, under the action of the above-mentioned active compounds.

Furthermore, the compounds of the formula I have proved effective in the treatment of rheumatic disorders and of myelopathy. It is particularly advantageous in this connection that these active compounds are active both against the pain associated therewith and positively affect the inflammatory processes occurring in rheumatic disorders and thus contribute to an improvement in the general condition of the patient. In this context, it has been advantageously shown that normal motoricity of the gastrointestinal tract is not adversely affected.

In all indication areas described here, in particular the use of N-methyl-N-[(1S)-1-phenyl-2-((3S)-3-hydroxypyrrolidin-1-yl)ethyl]-2,2-diphenylacetamid hydrochloride as a medicament has emerged as particularly effective in all sorts of preparation forms.

It has proved particularly advantageous additionally in the case of the compounds according to the invention that they obviously cannot pass through the blood-brain barrier on account of their structure and therefore exhibit no dependence potential. Also, until now no actions have been found which would restrict the use of the advantageous actions for the claimed indications in any way.

The compounds of the general formula I and their physiologically acceptable salts can therefore be used for the production of pharmaceutical preparations by bringing them into the suitable dose form together with at least one excipient or auxiliary and, if desired, with one or more further active compounds. The preparations thus obtained can be employed as medicaments in human or veterinary medicine. Suitable excipients are organic or inorganic substances which are suitable for enteral (e.g. oral or rectal) or parenteral administration and do not react with the novel compounds, for example water, vegetable oils, benzyl alcohols, polyethylene glycols, glycerol triacetate and other fatty acid glycerides, gelatin, soya lecithin, carbohydrates such as lactose or starch, magnesium stearate, talc or cellulose.

For oral administration, in particular tablets, coated tablets, capsules, syrups, juices or drops are used. Of interest are especially coated tablets and capsules having enteric coatings or capsule shells. For rectal administration, suppositories are used, and for parenteral administration, solutions, preferably oily or aqueous solutions, and also suspensions, emulsions or implants are used.

The active compounds claimed according to the invention can also be lyophilized and the lyophilisates obtained used, for example, for the production of injection preparations.

The preparations indicated can be sterilized and/or contain auxiliaries such as preservatives, stabilizers and/or wetting agents, emulsifiers, salts for affecting the osmotic pressure, buffer substances, colorants and/or flavorings. If desired, they can also contain one or more further active compounds, e.g. one or more vitamins, diuretics or anti-inflammatories.

The compounds of the formula I according to the invention are generally administered in analogy to other known preparations available commercially for the indications claimed, preferably in doses of from about 1 mg to 50 mg, in particular from 5 to 30 mg, per dose unit. The daily dose is preferably from about 0.02 to 20 mg/kg, in particular from 0.2 to 0.4 mg/kg of body weight.

The specific dose for each individual patient depends, however, on all sorts of factors, for example on the activity of the specific compound employed, on the age, body weight, general state of health and sex, on the diet, on the time and route of administration, and on the excretion rate, pharmaceutical combination and severity of the particular disorder to which the therapy applies. Oral administration is preferred.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application No. 195 23 502.9, filed Jun. 28, 1996 are hereby incorporated by reference.

EXAMPLES

In the following, examples are given which serve to illustrate the invention, but do not restrict the invention to the examples given. In the following text all temperatures are indicated in °C.

Example 1

N-Methyl-N-[(1S)-1-phenyl-2-((3S)-3-hydroxypyrrolidin-1-yl)ethyl]-2,2-diphenylacetamide, hydrochloride 22g of (2S)-2-N-carboxyethyl-2-phenylglycine-N,N-[(3S)-3-hydroxytetramethylamide] are initially introduced into a 500 ml apparatus and dissolved in 150 ml of tetrahydrofuran. While stirring, a solution consisting of 150 ml of tetrahydrofuran and 24.1 g of diphenylacetyl chloride is added dropwise at 10–20° C. in the course of one hour, a precipitate being formed at the start which, however, goes into solution again in the course of the reaction. Towards the end of the reaction a precipitate is again formed. The mixture is stirred at room temperature for a further 12 hours. It is then cooled to about 5° C. and the precipitated product is filtered off with suction. The separated product is washed with about 100 ml of tetrahydrofuran and dried. In this way, 39 g of crude product are obtained. This is recrystallized using about 250 ml of ethanol and 1 g of active carbon. Yield 33 g (73.2% of theory)

The pharmaceutical activity of the substances according to the invention in the treatment of inflammatory bowel disorders was investigated by a method described in *European J. of Pharmacology* 271 (1994) 245–251. The action of peripherally acting kappa-agonists on the activity of nerves supplying the large intestine, both of the healthy and of the inflamed large intestine, was investigated. For this purpose, the responses to cyclic pressure changes of a total of fourteen sensory nerve fibers were determined, of which eight were C fibers (slowly conducting) and six A fibers (rapidly conducting).

Inflammations in the intestinal region were produced by administration of trinitrobenzenesulphonic acid. The measurements were carried out four days after the administration of this substance.

The action of N-methyl-N-[(1S)-1-phenyl-2-((3S)-3-hydroxypyrrolidine-1-yl)ethyl]-2,2-diphenylacetamide hydrochloride on the nerve discharges was compared by example with that of the standard comparison substance ICI 204,488. N-Methyl-N-[(1S)-1-phenyl-2-((3S)-3-hydroxypyrrolidin-1-yl)ethyl]-2,2-diphenylacetamide hydrochloride inhibited the nerve response to the cyclic pressure increases in a dose-dependent manner. In the non-inflamed large intestine, the response was inhibited by 75.4% after administration of a total of 32 mg/kg. In the inflamed intestine, this dose actually inhibited the action by 99.8%. The $ED_{50}$ values of N-methyl-N-[(1S)-1-phenyl-2-((3S)-3-hydroxypyrrolidin-1-yl)ethyl]-2,2-diphenylacetamide hydrochloride were 13±4 mg/kg in the non-inflamed large intestine. In comparison, ICI 204,488 was without action even after administration of a total of 32 mg/kg.

The inhibitory action of N-methyl-N-[(1S)-1-phenyl-2-((3S)-3-hydroxypyrrolidin-1-yl)ethyl]-2,2-diphenylacetamide hydrochloride is therefore obviously produced by the activation of kappa-opioid receptors on the sensory nerve ends, while ICI 204,488 has no action on these receptors.

The following examples relate to pharmaceutical preparations:

Example A: Injection vials

A solution of 100 g of an active compound of the formula I and 5 g of disodium hydrogen phosphate are adjusted to pH 6.5 in 3 l of double-distilled water using 2N hydrochloric acid, sterile filtered, filled into injection vials, lyophilized under sterile conditions and aseptically sealed. Each injection vial contains 5 mg of active compound.

Example B: Suppositories

A mixture of 20 g of an active compound of the formula I is fused with 100 g of soya lecithin and 1400 g of cocoa butter, poured into molds and allowed to cool. Each suppository contains 20 mg of active compound.

Example C: Solution

A solution is prepared from 1 g of an active compound of the formula I, 9.38 g of $NaH_2PO_4 \cdot 2H_2O$, 28.48 g of $NA_2HPO_4 \cdot 12H_2O$ and 0.1 g of benzalkonium chloride in 940 ml of double-distilled water. The solution is adjusted to pH 6.8, made up to 1 l and sterilized by irradiation.

Example D: Ointment 500 mg of an active compound of the formula I are mixed with 99.5 g of petroleum jelly under aseptic conditions.

Example E: Tablets

A mixture of 1 kg of active compound of the formula I, 4 kg of lactose, 1.2 kg of potato starch, 0.2 kg of talc and 0.1 kg of magnesium stearate is compressed in a customary manner to give tablets in such a way that each tablet contains 10 mg of active compound.

Example F: Coated tablets

Analogously to Example E, tablets are pressed which are then coated in a customary manner with a coating of sucrose, potato starch, talc, tragacanth and colorant.

Example G: Capsules 2 kg of active compound of the formula I are filled into hard gelatin capsules in the customary manner such that each capsule contains 20 mg of the active compound.

Example H: Ampoules

A solution of 1 kg of active compound of the formula I in 60 l of double-distilled water is sterile filtered, filled into ampoules, lyophilized under sterile conditions and aseptically sealed. Each ampoule contains 10 mg of active compound.

What is claimed is:

1. A method for the treatment of inflammatory bowel disorders, which comprises administering an effective amount of a composition exhibiting kappa-opiate agonist activity which composition comprises a physiologically acceptable excipient or auxiliary and a compound of the formula I

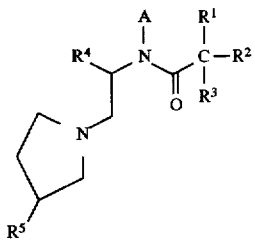

in which
R$^1$ is Ar, cycloalkyl having 3–7 C atoms or cycloalkylalkyl having 4–8 C atoms,
R$^2$ is Ar, or
R1 and R$^2$ together are

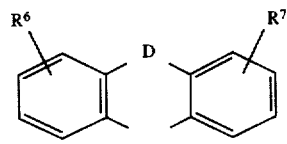

R$^3$ is H, OH, OA or A,
R$^4$ is A or phenyl which is optionally mono- or disubstituted by Hal, OH, OA, CF$_3$, NO$_2$, NH$_2$, NHA, NHCOA, NHSO$_2$A and/or NA$_2$,
R$^5$ is OH, CH$_2$OH,
R$^6$ and R$^7$ in each case independently of one another are H, Hal, OH, OA, CF$_3$, NH$_2$, NHA, NA$_2$, NHCOA, NHCONH$_2$, NO$_2$ or methylenedioxy with the oxy groups bonded to adjacent carbons on the ring,
A is alkyl having 1–7 C atoms,
Ar is a mono- or bicyclic aromatic radical optionally containing an N, O or S atom in the ring and optionally mono-, di- or trisubstituted by A, Hal, OH, OA, CF$_3$, NH$_2$, NHA, NA$_2$, NHCOA and/or NHCONH$_2$,
D is CH$_2$, O, S, NH, NA, —CH$_2$—CH$_2$—, —CH=CH—, —CH$_2$NH—, —CH$_2$—NA— or a bond and Hal is F, Cl, Br or I; a physiologically acceptable salt thereof or a glycosylated derivative thereof.

2. A method according to claim 1, wherein in the compound of formula I, Ar is phenyl, R$^3$ is H and A is methyl.

3. A method according to claim 1, wherein in the compound of formula I, R$^1$ is Ar, R$^2$ is Ar and R$^5$ is OH.

4. A method according to claim 1, wherein in the compound of formula I, R$^1$ is phenyl, R$^2$ is phenyl, R$^4$ is phenyl, R$^5$ is OH and A is methyl.

5. A method according to claim 1, wherein the compound of formula I is N-methyl-N-[(1S)-1-phenyl-2-((3S)-3-hydioxypyrrolidin-1-yl)-ethyl]-2,2-diphenyl-acetamide hydrochloride.

6. The method of claim 1, wherein the compound of formula I, a physiologically acceptable salt thereof or a glycosylated derivative thereof is effective for normalizing a disorder of intestinal motoricity.

* * * * *